US008684252B2

(12) United States Patent
Patel et al.

(10) Patent No.: US 8,684,252 B2
(45) Date of Patent: *Apr. 1, 2014

(54) SURGICAL STAPLING INSTRUMENT (71) Applicant: Covidien LP, Mansfield, MA (US)

(72) Inventors: Nihir Patel, Stamford, CT (US); Guido Pedros, Seymour, CT (US); Stephen R. Paul, East Hartford, CT (US); Keith L. Milliman, Bethel, CT (US); Ryan Williams, Milford, CT (US); Michael J. Havrilko, Shelton, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/667,343

(22) Filed: Nov. 2, 2012

(65) Prior Publication Data

US 2013/0056517 A1 Mar. 7, 2013

Related U.S. Application Data (63) Continuation of application No. 12/899,113, filed on Oct. 6, 2010, now Pat. No. 8,322,590.

(60) Provisional application No. 61/255,544, filed on Oct. 28, 2009.

(51) Int. Cl.
*A61B 17/04* (2006.01)
*A61B 17/10* (2006.01)

(52) U.S. Cl.
USPC ..................................... 227/179.1; 227/176.1

(58) Field of Classification Search
USPC .................... 227/175.1–182.1; 606/142–143; 403/348–349
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |

(Continued)

FOREIGN PATENT DOCUMENTS

| | | |
|---|---|---|
| CA | 908529 | 8/1972 |
| DE | 1057729 | 5/1959 |

(Continued)

*Primary Examiner* — Robert Long (57) ABSTRACT

A surgical stapling instrument comprising a handle assembly having a proximal end, an elongated body portion extending distally from the handle assembly, a head portion disposed adjacent a distal portion of the elongated body portion and including an anvil assembly and a shell assembly. The shell assembly includes a shell and a staple guide housing a plurality of staples. A flexible engagement structure attaches the staple guide to the shell.

16 Claims, 12 Drawing Sheets

(56) References Cited

U.S. PATENT DOCUMENTS

| | | |
|---|---|---|
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |

(56) References Cited

U.S. PATENT DOCUMENTS

| | | |
|---|---|---|
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 7,032,798 B2 | 4/2006 | Whitman et al. |
| 7,059,331 B2 | 6/2006 | Adams et al. |
| 7,059,510 B2 | 6/2006 | Orban, III |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,303,106 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,717,313 B2 | 5/2010 | Criscuolo et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,080 B2 | 11/2010 | Schwemberger |
| 7,845,536 B2 | 12/2010 | Viola et al. |
| 2001/0000903 A1 | 5/2001 | Heck et al. |
| 2001/0010320 A1 | 8/2001 | Bolduc et al. |
| 2001/0054636 A1 | 12/2001 | Nicolo |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0144675 A1 | 7/2003 | Nicolo |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2005/0051597 A1 | 3/2005 | Tolendano |
| 2005/0067454 A1 | 3/2005 | Vresh et al. |
| 2005/0087580 A1 | 4/2005 | Orban, III |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |

(56) References Cited

U.S. PATENT DOCUMENTS

| | | |
|---|---|---|
| 2006/0047308 A1 | 3/2006 | Ortiz et al. |
| 2006/0085032 A1 | 4/2006 | Viola |
| 2006/0085033 A1 | 4/2006 | Criscuolo et al. |
| 2006/0085034 A1 | 4/2006 | Bettuchi |
| 2006/0085035 A1 | 4/2006 | Viola |
| 2006/0097025 A1 | 5/2006 | Milliman et al. |
| 2006/0108393 A1 | 5/2006 | Heinrich et al. |
| 2006/0144897 A1 | 7/2006 | Jankowski et al. |
| 2006/0151567 A1 | 7/2006 | Roy |
| 2006/0191975 A1 | 8/2006 | Adams et al. |
| 2006/0201989 A1 | 9/2006 | Ojeda |
| 2006/0201993 A1 | 9/2006 | Hur |
| 2006/0241692 A1 | 10/2006 | McGuckin, Jr. et al. |
| 2006/0255090 A1 | 11/2006 | Milliman et al. |
| 2006/0289601 A1 | 12/2006 | Orban, III |
| 2007/0023475 A1 | 2/2007 | Csiky |
| 2007/0027473 A1 | 2/2007 | Vresh et al. |
| 2007/0029363 A1 | 2/2007 | Popov |
| 2007/0034666 A1 | 2/2007 | Holsten et al. |
| 2007/0034667 A1 | 2/2007 | Holsten et al. |
| 2007/0034668 A1 | 2/2007 | Holsten et al. |
| 2007/0038248 A1 | 2/2007 | Heinrch |
| 2007/0060952 A1 | 3/2007 | Roby et al. |
| 2009/0212088 A1 | 8/2009 | Okada et al. |
| 2009/0230170 A1 | 9/2009 | Milliman |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |
| 2009/0236398 A1 | 9/2009 | Cole et al. |
| 2009/0236400 A1 | 9/2009 | Cole et al. |
| 2009/0236401 A1 | 9/2009 | Cole et al. |
| 2009/0242612 A1 | 10/2009 | Adams et al. |
| 2009/0250502 A1 | 10/2009 | Milliman |
| 2009/0255976 A1 | 10/2009 | Marczyk et al. |
| 2009/0302089 A1 | 12/2009 | Harari et al. |
| 2009/0321496 A1 | 12/2009 | Holsten et al. |
| 2010/0001036 A1 | 1/2010 | Marczyk et al. |
| 2010/0001037 A1 | 1/2010 | Racenet et al. |
| 2010/0019016 A1 | 1/2010 | Edoga et al. |
| 2010/0025452 A1 | 2/2010 | Whitman |
| 2010/0038401 A1 | 2/2010 | Milliman et al. |
| 2010/0051668 A1 | 3/2010 | Milliman et al. |
| 2010/0059571 A1 | 3/2010 | Chen et al. |
| 2010/0065607 A1 | 3/2010 | Orban, III et al. |
| 2010/0065609 A1 | 3/2010 | Schwemberger |
| 2010/0084453 A1 | 4/2010 | Hu |
| 2010/0089971 A1 | 4/2010 | Milliman et al. |
| 2010/0096435 A1 | 4/2010 | Fuchs et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0127039 A1 | 5/2010 | Hessler et al. |
| 2010/0133319 A1 | 6/2010 | Milliman et al. |
| 2010/0147923 A1 | 6/2010 | D'Agostino et al. |
| 2010/0155452 A1 | 6/2010 | Csiky |
| 2010/0155454 A1 | 6/2010 | Viola |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0237132 A1 | 9/2010 | Measamer et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0276471 A1 | 11/2010 | Whitman |
| 2010/0282813 A1 | 11/2010 | Milliman |
| 2010/0282815 A1 | 11/2010 | Bettuchi et al. |
| 2010/0301098 A1 | 12/2010 | Kostrzewski |

FOREIGN PATENT DOCUMENTS

| | | |
|---|---|---|
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| FR | 1461464 | 12/1966 |
| FR | 1588250 | 4/1970 |
| FR | 2443239 | 12/1979 |
| GB | 1185292 | 3/1970 |
| GB | 2016991 | 9/1979 |
| GB | 2070499 | 9/1981 |
| NL | 7711347 | 10/1977 |
| WO | 8706448 | 11/1987 |
| WO | 8900406 | 1/1989 |
| WO | 9006085 | 6/1990 |

SURGICAL STAPLING INSTRUMENT

CROSS REFERENCE TO RELATED APPLICATION

The present application is a Continuation Application of U.S. application Ser. No. 12/899,113, filed Oct. 6, 2010, which claims priority from Provisional Application Ser. No. 61/255,544, filed Oct. 28, 2009, the entire contents of which are incorporated herein by reference.

This application claims priority from provisional application Ser. No. 61/255,544, filed Oct. 28, 2009, the entire contents of which are incorporated herein by reference.

BACKGROUND

1. Technical Field

The present disclosure relates generally to a surgical stapling device for applying surgical staples to body tissue. More particularly, the present disclosure relates to a surgical stapling device suitable for performing circular anastomosis and/or treatment to internal walls of hollow tissue organs.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 7,303,106 6,945,444, 6,053,390, 5,588,579, 5,119,983, 5,005,749, 4,646,745, 4,576,167, and 4,473,077. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil. An annular knife is concurrently advanced to core tissue within the hollow organ to free a tubular passage within the organ.

Besides anastomosis of hollow organs, surgical stapling devices for performing circular anastomosis have been used to treat internal hemorrhoids in the rectum. Typically, during use of a circular stapling device for hemorrhoid treatment, the anvil head and the staple holding component of the surgical stapling device are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling device is fired to remove the hemorrhoidal tissue and staple the cut tissue. In hemorrhoidectomy, the hemorrhoids are removed. Stapled hemorrhoidopexy is a surgical procedure in which the stapling device is used to remove tissue just above the hemorrhoids in order to pull the hemorrhoids back up inside the rectum and reduce the symptoms. The staples interrupt the blood flow of the superior hemorrhoidal arterial branches, cutting off the blood supply to the tissue, thus causing the hemorrhoids to shrink.

Several known circular staplers have a shell assembly which contains a stapler pusher and a staple guide which houses a plurality of staples in a plurality of annular rows. The staple guide in certain of these instruments is ultrasonically welded to the shell assembly. Although effective, alternative attachment methods could be advantageous from a securement and a manufacturing standpoint.

SUMMARY

The present disclosure provides in one aspect a surgical stapling instrument including a handle assembly, an elongated body portion, and a head portion. The head portion is disposed adjacent a distal portion of the elongated body portion and includes an anvil assembly and a shell assembly. The shell assembly includes a shell and a staple guide housing a plurality of staples. A flexible engagement structure attaches the staple guide to the shell.

In one embodiment, the flexible engagement structure includes at least one hook on the staple guide. The shell can include a locking aperture configured and dimensioned to receive the hook of the staple guide.

In another embodiment, the flexible engagement structure includes a flexible tab on the shell. The flexible tab can include an aperture to receive a hook on the staple guide. The hook can be substantially rigid.

In another embodiment, the shell assembly includes a plurality of projections extending distally to apply a distal force to the staple guide. The projections can be compressible by the staple guide.

The present disclosure provides in another aspect a surgical stapling instrument comprising a handle assembly including a movable handle for actuating the stapler, an elongated body portion extending distally from the handle assembly, and a head portion disposed adjacent a distal portion of the elongated body portion and including an anvil assembly and a shell assembly. The shell assembly includes a shell and a staple guide housing a plurality of staples. The staple guide includes a tab and the shell assembly includes a slotted region having a first slotted portion and a second slotted portion angled with respect to the first slotted portion. The tab is movable within the slotted region to attach the staple guide and shell assembly.

In one embodiment, the first slotted region extends substantially axially and the second slotted region extends substantially radially. In one embodiment, the second slotted region has a reduced diameter section having a dimension smaller than an outer dimension of the tab.

DESCRIPTION OF THE DRAWINGS

Various embodiment of the presently disclosed surgical stapling device are disclosed herein with reference to the drawings, wherein.

DETAILED DESCRIPTION OF EMBODIMENTS

Embodiments of the presently disclosed surgical stapling instrument will now be described in detail with reference to the drawings in which like reference numerals designate identical or corresponding elements in each of the several views.

Throughout this description, the term "proximal" will refer to the portion of the instrument closer to the operator and the term "distal" will refer to the portion of the instrument further from the operator.

Figure 1:
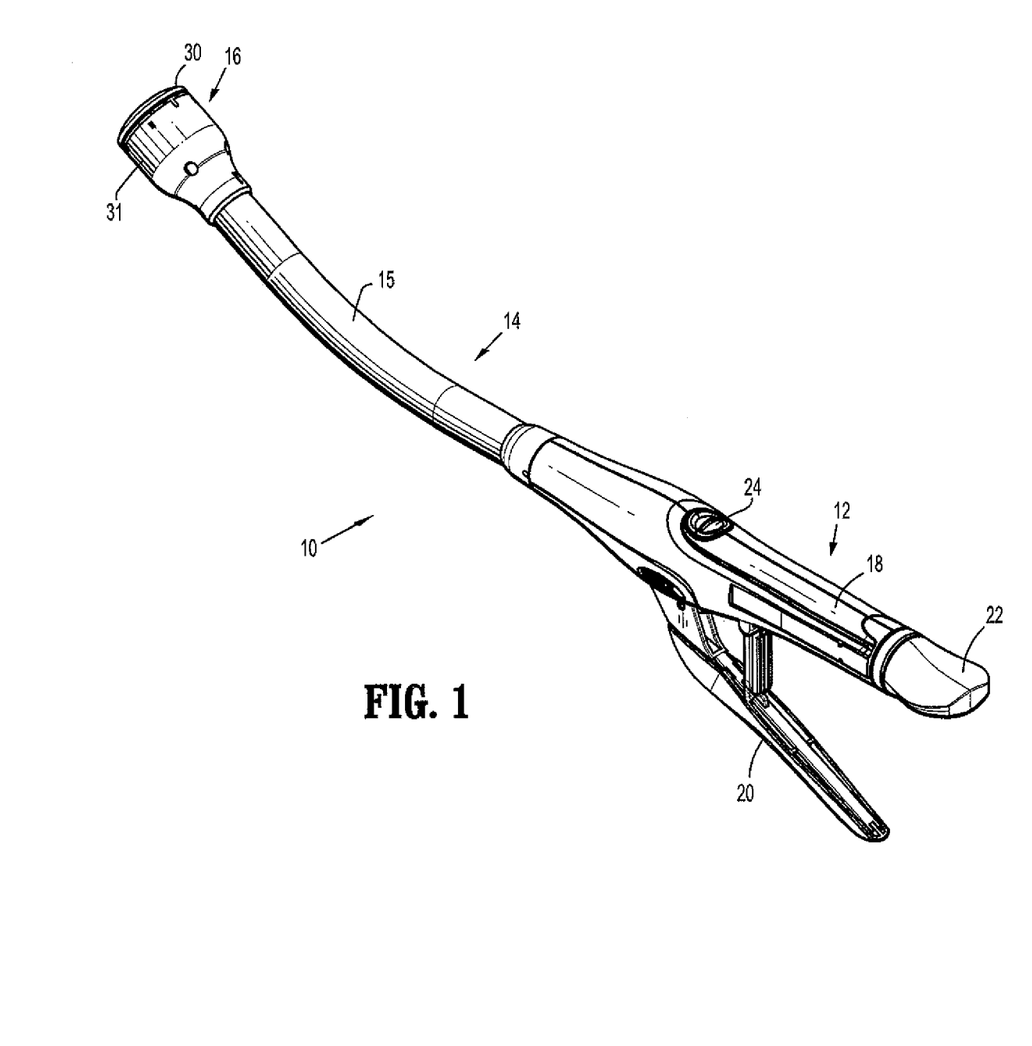
FIG. 1 is a perspective view of an embodiment of the presently disclosed surgical stapling instrument in an approximated position.

With initial reference to FIG. 1, an embodiment of the presently disclosed surgical stapling device is shown generally as reference number 10. Briefly, surgical stapling device 10 includes a handle assembly 12, an elongated body portion 14 including a curved elongated outer tube 15 extending from handle assembly 12, and a head portion 16 extending from outer tube 15. Alternately, in some surgical procedures, e.g., the treatment of hemorrhoids, the body portion can be substantially straight. The length, shape and/or the diameter of body portion 14 and head portion 16 may also be varied to suit a particular surgical procedure.

In the illustrated embodiments, handle assembly 12 includes a stationary handle 18, a firing trigger 20, a rotatable approximation knob 22 and an indicator 24. Head portion 16 includes an anvil assembly 30 and a shell assembly 31. Anvil assembly 30 is movable in relation to shell assembly 31 between spaced (unapproximated) and approximated positions. Anvil assembly includes an anvil shaft mounted (preferably removably mounted) to an anvil retainer of the surgical stapling instrument 10.

In operation, rotation of approximation knob 22 causes movement of anvil assembly 30 in relation to shell assembly 31 between spaced and approximated positions, as approximation knob 22 is mechanically engaged with an anvil retainer via bands which is connected to anvil assembly 30. It is envisioned that rotation of approximation knob 22 in a first direction (e.g., clockwise) causes proximal movement of anvil assembly 30 to an approximated position to clamp tissue between the anvil and shell assemblies and rotation of approximation knob 22 in a second opposite direction (e.g., counter-clockwise) causes distal movement of anvil assembly 30 to an unapproximated position.

Actuation of firing trigger 20 (i.e., pivoting in the direction toward the stationary handle 18), causes staples to be ejected from shell assembly 31 towards anvil assembly 30. That is, firing trigger 20 is disposed in mechanical cooperation with a staple pusher or pusher back 50 (FIG. 2) such that actuation of firing trigger 20 causes advancement of pusher 50 through the staple guide 60 and into contact with the staples 70 housed in an annular array(s) in staple guide 60. This forces the staples 70 out of staple pockets or slots 33 into staple deforming pockets of anvil assembly 30. Pusher 50 includes a plurality of distally extending pusher fingers 52 which contact the staples 70 to advance them into contact with the anvil. A circular knife 74 is frictionally retained with the central throughbore 51 of pusher back 50 to fixedly secure knife 74 in relation to pusher back 50. Knife 74 is advanceable with the pusher back 50 to sever tissue between the annular rows of staples 70. Throughbore 51 is slidably positioned about inner guide portion 35 of shell 31. Distal cylindrical section 53 of pusher 50 is slidably positioned within distal cylindrical section 34 of shell 31. The proximal end of pusher back 50 includes members 55 which are configured to lockingly engage with a pusher link (not shown). Shell 31 can also include vent holes 32.

Further details of the features of surgical stapling device 10, such as the approximation assembly and firing assembly, are disclosed in commonly-owned U.S. Pat. Nos. 7,303,106, 7,234,624 and 7,168,604, the entire contents of which are incorporated by reference herein.

FIGS. 2-12 illustrate a first embodiment of the flexible engagement structure for attaching the staple guide 60 to the shell assembly 31. With initial reference to FIGS. 3 and 4, a flexible hook 80 on an outer surface of staple guide 60 extends in a proximal direction, preferably terminating at the proximal end of staple guide 60. The hook 80 is proximal of flange 61 of staple guide 60. The hook can be substantially flush with the outer surface 63 of staple guide 60. Hook 80 has an angled proximal surface 82, angled with respect to a longitudinal or axial region 89 extending from the staple guide 60. The hook 80 is preferably formed integrally with the staple guide 60, however, alternatively, it could be a separate element(s) attached to the staple guide 60. Two or more hooks are preferably provided to engage at spaced regions along the shell 31. For example two hooks can be placed approximately 180 degrees apart, three hooks at approximately 120 degrees apart, etc. The illustrated embodiment shows four hooks 80 spaced approximately 90 degrees apart. Other spacings, including non-equidistant spacings of the hooks, are also contemplated.

Figure 5:
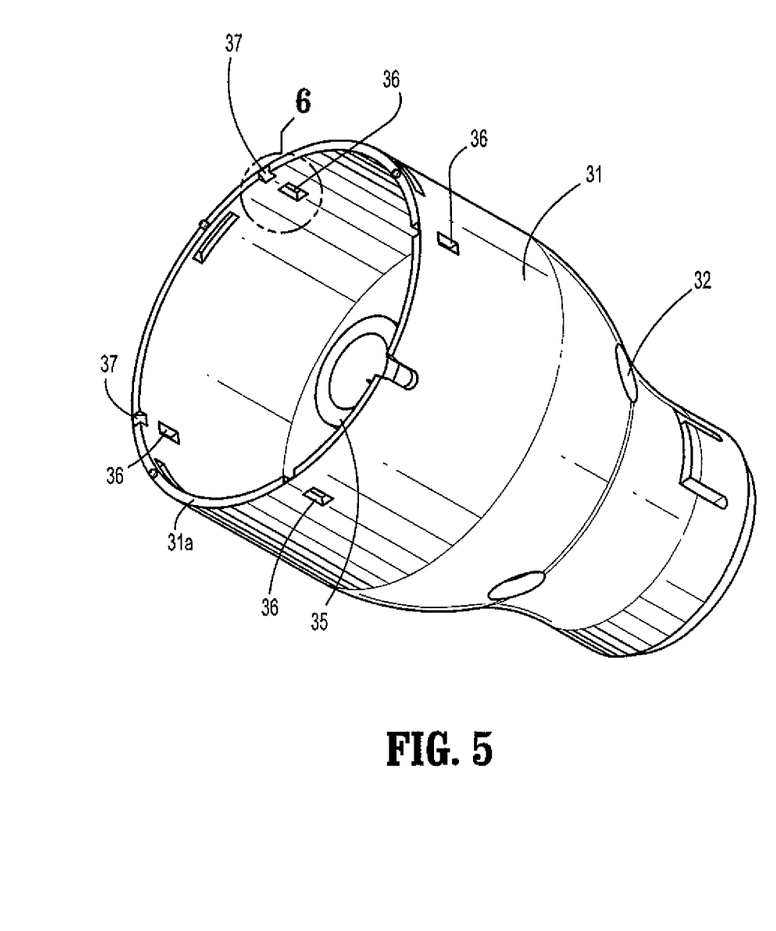
FIG. 5 is an enlarged view of the shell of FIGS. 1 and 2.
Figure 6:
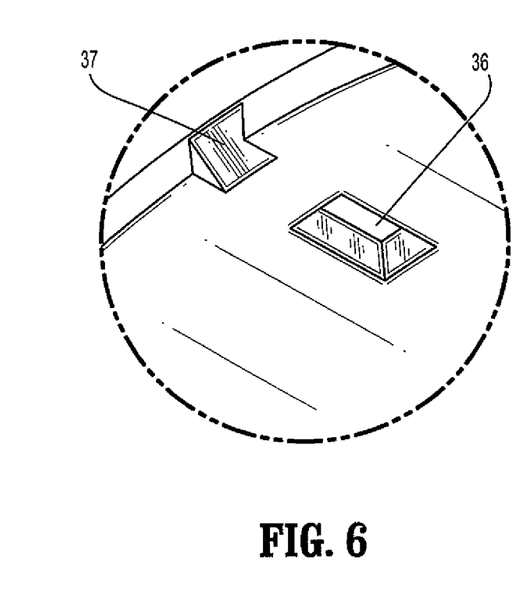
FIG. 6 is an enlarged view of the area of detail designated in FIG. 5 showing the ramp and locking aperture.
Figure 7:
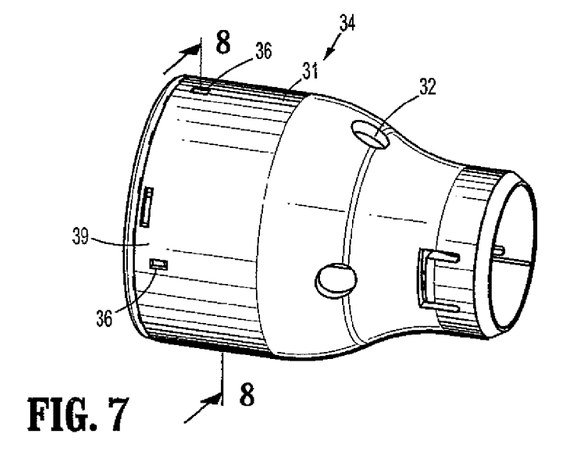
FIG. 7 is a side perspective view of the shell assembly of FIG. 2.
Figure 8:
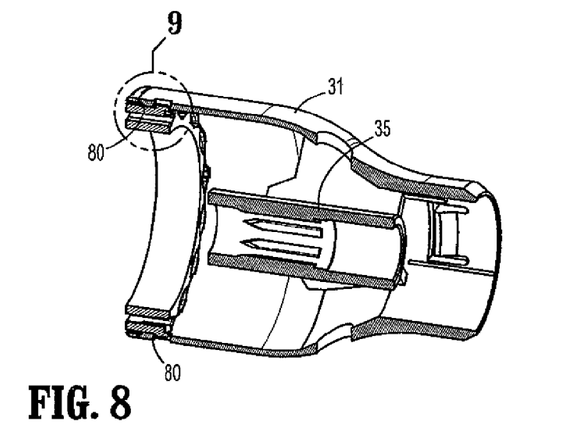
FIG. 8 is a sectional view of the shell assembly of FIG. 7 taken along lines 8-8 of FIG. 7.
Figure 9:
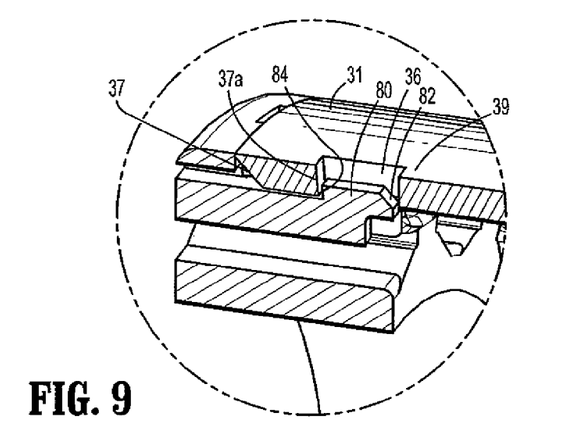
FIG. 9 is a close up view in cross section of the area of detail designated in FIG. 8 showing engagement of the flexible hook of the staple guide with the locking aperture of the shell.

Referring to FIGS. 5, 6 and 9, shell assembly 31 includes locking apertures 36, preferably spaced slightly proximally from the distal edge 31a of shell 31, each configured and dimensioned to receive a hook 80. Angled wall or ramp 37 on the inner wall of the shell 31 facilitates hook engagement as described below.

Figure 10:
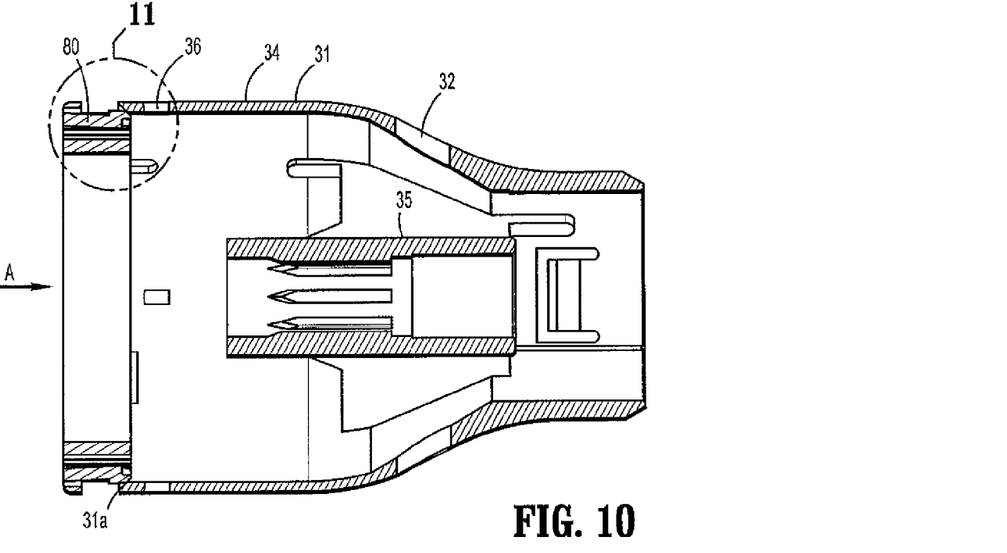
FIG. 10 is a cross sectional view of the shell assembly prior to attachment of the staple guide showing flexure of the flexible hook.
Figures 11, 12:
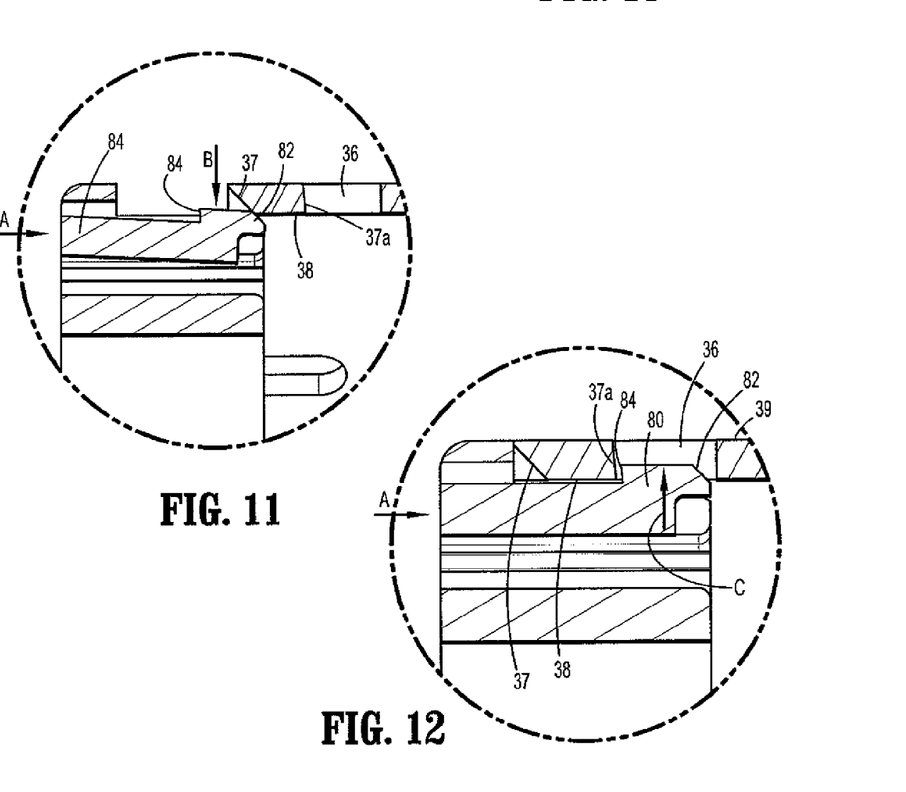
FIG. 11 is a close up view in cross section of the area of detail designated in FIG. 10.
FIG. 12 is a close up view similar to FIG. 11 showing engagement of the staple guide and shell in final assembly.
Figure 13:
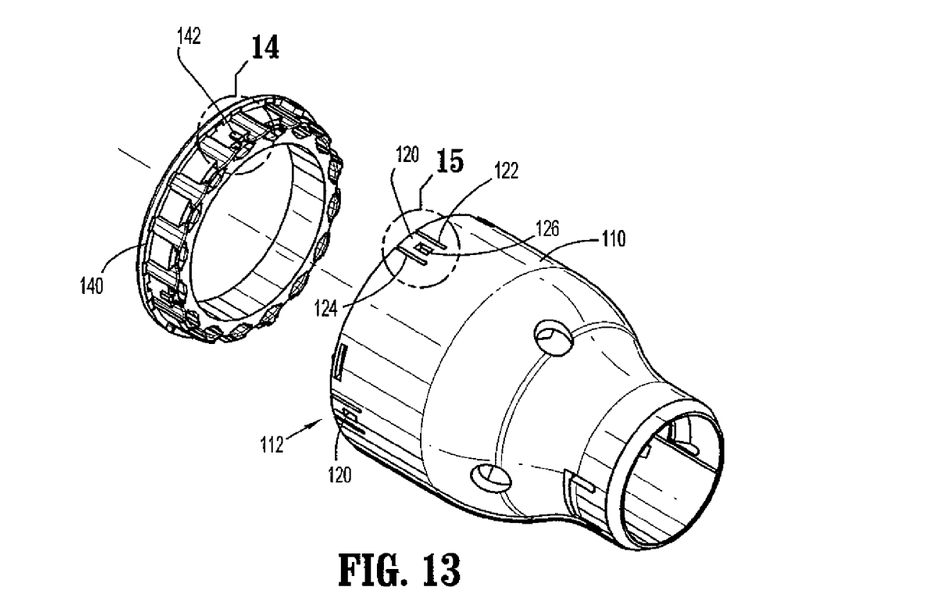
FIG. 13 is an exploded view of a shell assembly and staple guide of an alternate embodiment of the present disclosure.
Figure 14:
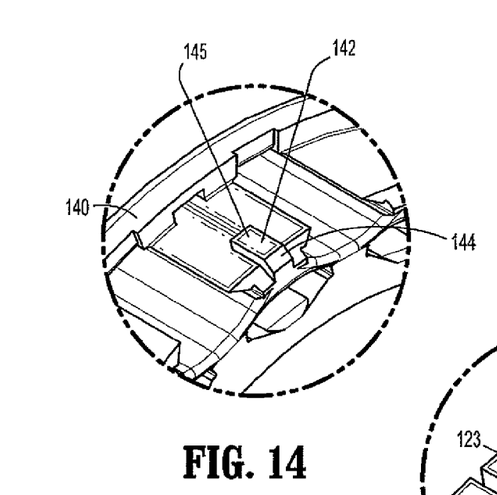
FIG. 14 is a close up view of the area of detail designated in FIG. 13 showing the rigid hook of the staple guide.
Figure 15:
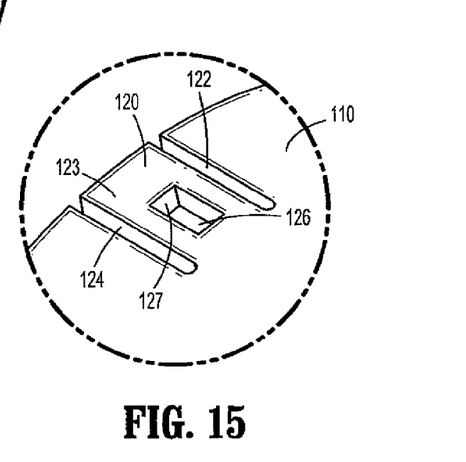
FIG. 15 is a close up view of the area of detail designated in FIG. 13 showing the engagement tab of the shell.

As can be appreciated by viewing FIGS. 10-12, during assembly when staple guide 60 is attached to the shell assembly 31 by placement in a direction of arrow A, each hook 80 initially flexes radially inwardly (downwardly in the orientation of FIG. 10) in the direction of arrow B as the surface of angled wall 37 of shell 31 is engaged by angled surface 82 of the hook 80 of staple guide 60. Upon sufficient distal advancement in manufacture in the direction of arrow A, the proximal end of hook 80 passes beyond angled surface 37 and beyond wall 38 and then being no longer biased radially inwardly (downwardly in the view of FIG. 11), can move radially outwardly (upwardly) in the direction of arrow C to its normal unstressed condition to extend within locking aperture 36. As shown, in this position, the engagement of shoulder 84 of hook 80 with wall surface 37a prevents distal movement of the staple guide 60 to retain it in position secured to the shell 31 (see also FIG. 9). During use, a distal force applied to the staple guide during manipulation of the instrument or firing of the staples will not dislodge the staple guide 60 from the shell assembly 31 since distal movement is prohibited by wall 37a. Each of the hooks 80 engages a corresponding locking aperture 36 in the same manner as described above. Note that preferably the hook 80 does not extend beyond the outer confines (outer diameter) of the aperture 36 so as to not extend past the outer surface 39 of shell 31.

In the alternate embodiment illustrated in FIGS. 13-17, a rigid hook is utilized. Shell 110 is identical to shell 31 of FIG. 2 except for the structure cooperating with the hooks of the staple guide. More specifically, shell 110 has a flexible tab 120 formed by cutouts 122, 124 in the distal end 112 of the shell 110. The flexible tab 120 has a locking aperture 126 formed therein. Staple guide 140 is identical to staple guide 60 of FIG. 2 except for the hook configuration. More specifically, staple guide 140 has a hook 142 formed thereon, which is preferably substantially rigid. As shown, the hook 142 extends proximally from staple guide 140 and at its proximal end has an angled proximal surface 144 and vertical surface 147 substantially perpendicular to a longitudinal axis of staple guide 140. A longitudinal or axial region 145 extends distally. A plurality of tabs 120 are provided in shell 110, each dimensioned and configured to receive a hook 142.

Figure 16:
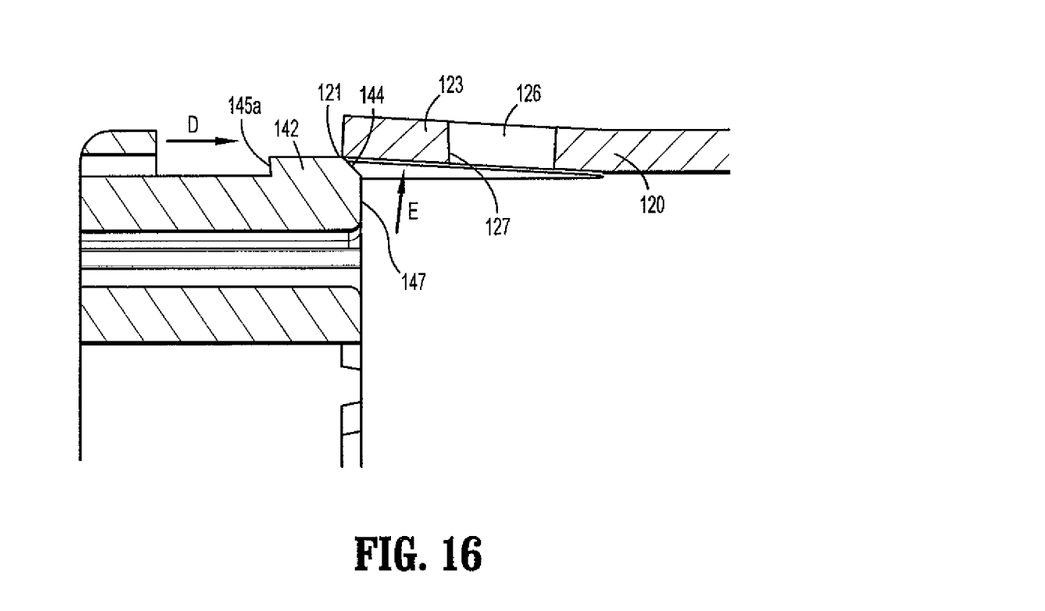
FIG. 16 is a close up cross-sectional view showing initial engagement of the staple guide and shell of FIG. 13 causing flexure of the hook.
Figure 17:
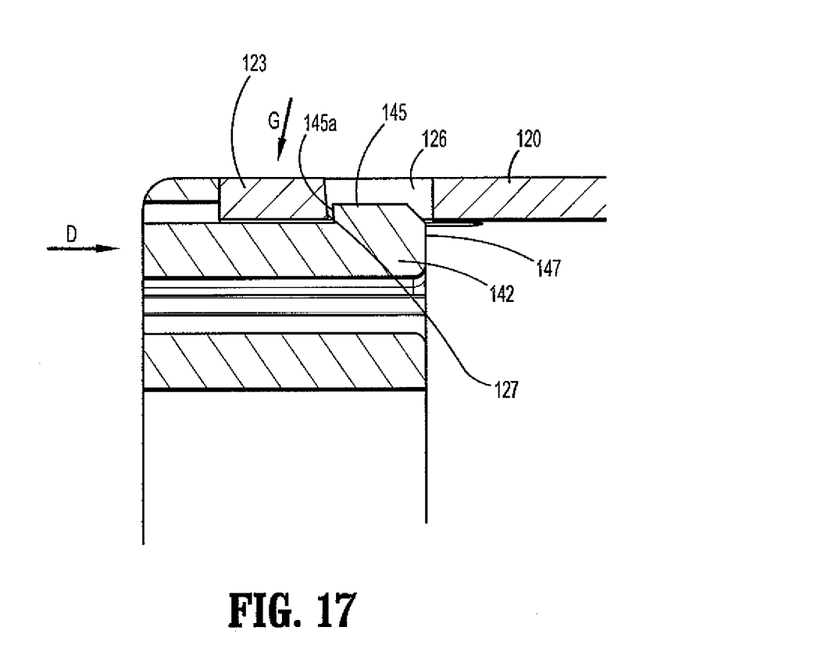
FIG. 17 is a close up cross-sectional view similar to FIG. 16 showing engagement of the staple guide and shell in final assembly.

As can be appreciated by viewing FIGS. 16 and 17, when staple guide 140 is attached during assembly to the shell assembly 110 by placement in a direction of arrow D, the tab 120 of the shell 110 initially flexes radially away (upwardly in the orientation of FIG. 16) away from the shell 110 in the direction of arrow E as angled surface 144 of hook 142 engages the edge 121 of distal tab portion 123 of the tab 120. The edge 121 can optionally be angled to engage the angled surface 142 of hook 140. Upon sufficient distal advancement in manufacture in the direction of arrow D, the angled wall 144 of hook 140 passes beyond edge 121 and beyond distal tab portion 123, and then the distal tab portion 123, no longer biased upwardly (radially), can move downwardly (inwardly toward the longitudinal axis) in the direction of arrow G toward the shell 110 so the hook 142 is seated within locking aperture 126. As shown, in this position, the engagement of shoulder 145a of hook 142 with wall 127 of distal tab portion 123 prevents distal movement of the staple guide 140 to retain it in position. During use, a distal force applied to the staple guide 140 during manipulation of the instrument or firing of the staples will not dislodge the staple guide 140 from the shell assembly 110 since distal movement is prohibited by wall 127.

Figure 18:
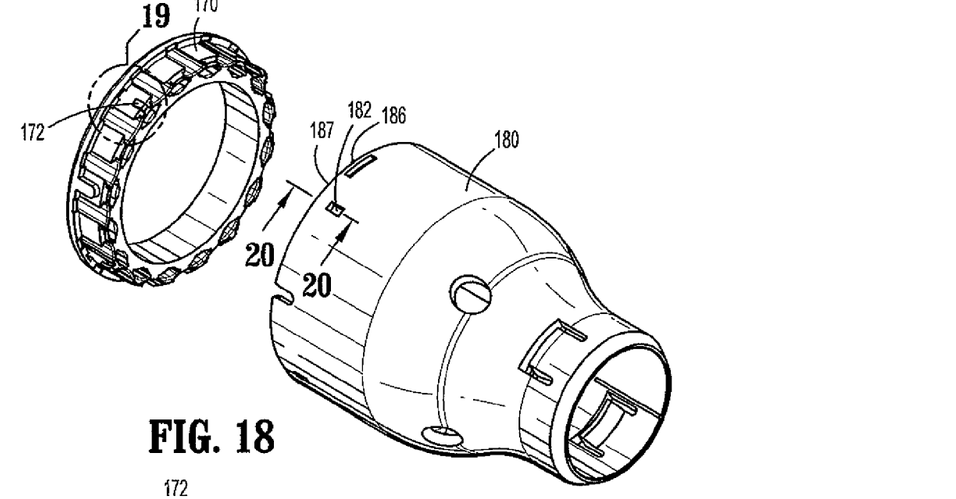
FIG. 18 is an exploded view of a shell and staple guide of another alternate embodiment of the present disclosure.
Figure 19:
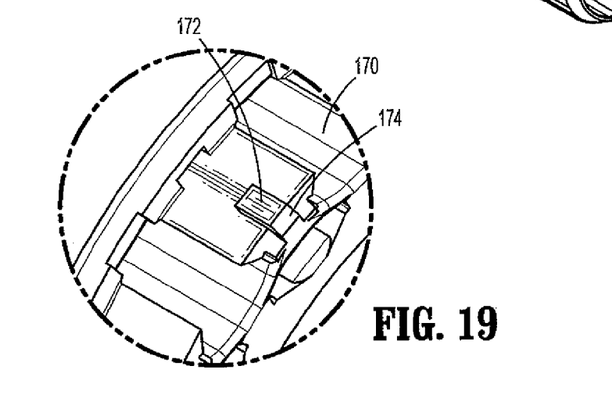
FIG. 19 is a close up view of the area of detail designated in FIG. 18 showing the hook of the staple guide.
Figure 20:
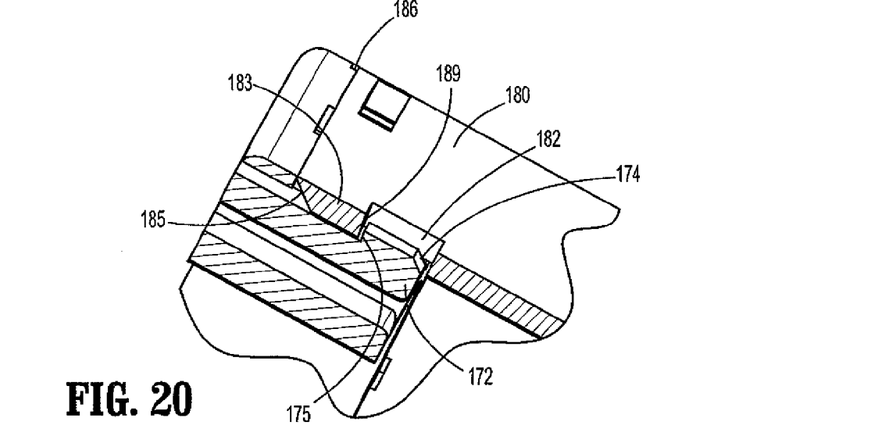
FIG. 20 is a close up cross-sectional view taken along 20-20 of FIG. 19 showing the engagement of the staple guide and shell in the final assembly.
Figure 21:
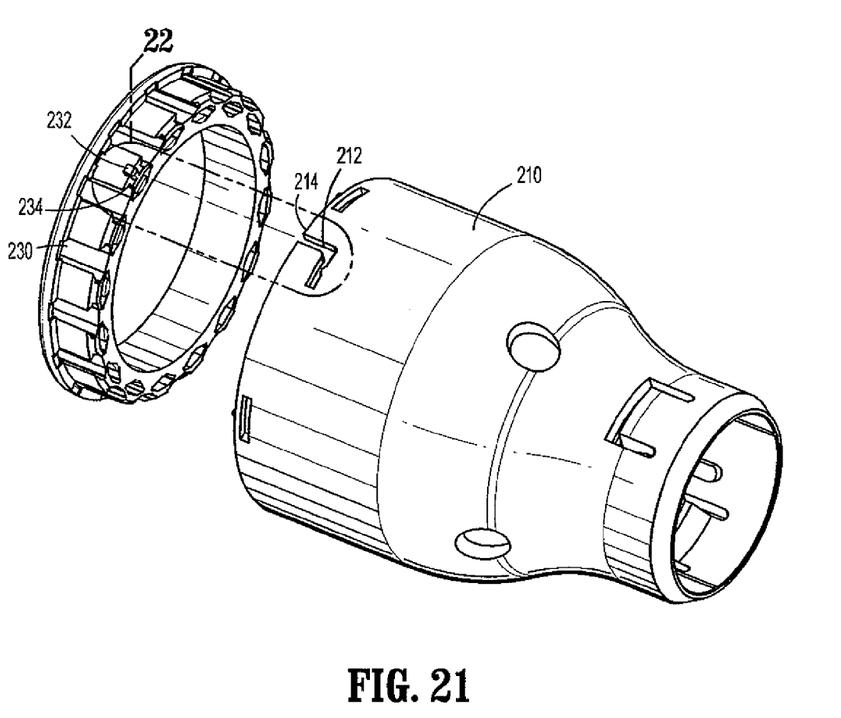
FIG. 21 is an exploded view of a shell and staple guide of another alternate embodiment of the present disclosure.
Figure 22:
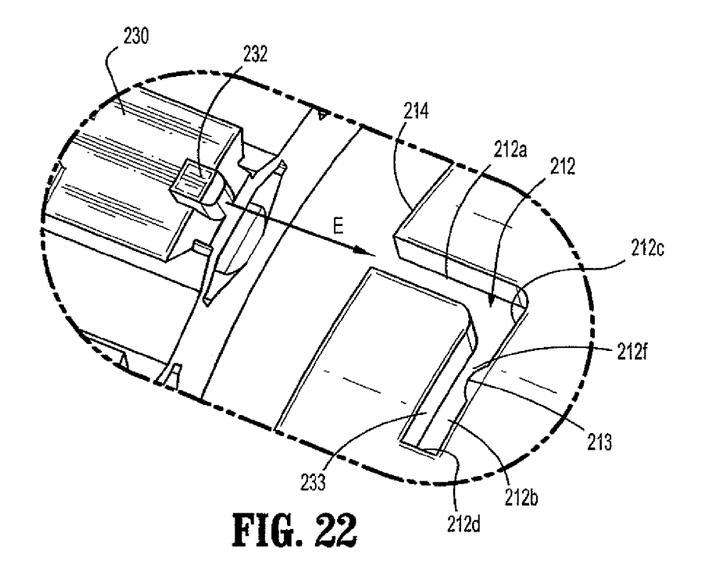
FIG. 22 is a close up view of the area of detail designated in FIG. 21.
Figure 23:
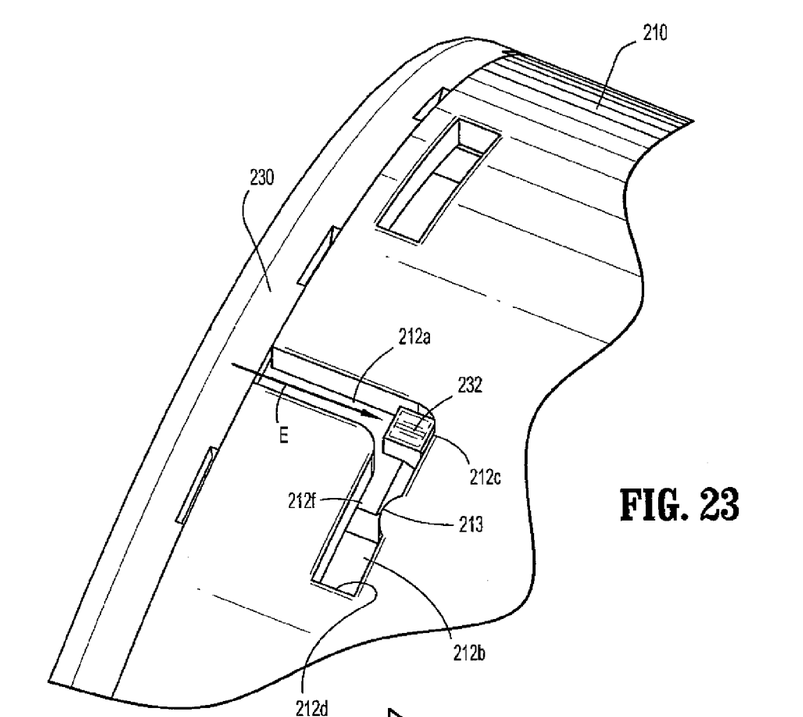
FIG. 23 is a close up view showing initial engagement of the locking tab of the staple guide of FIG. 21 in the slot of the shell.
Figure 24:
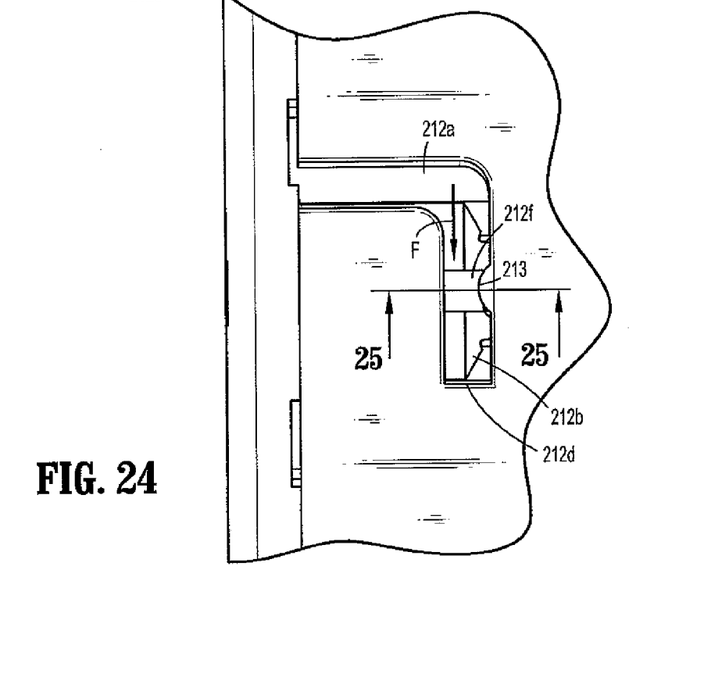
FIG. 24 is a close up view of the locking tab of FIG. 23 moving radially in the slot of the shell.
Figure 25:
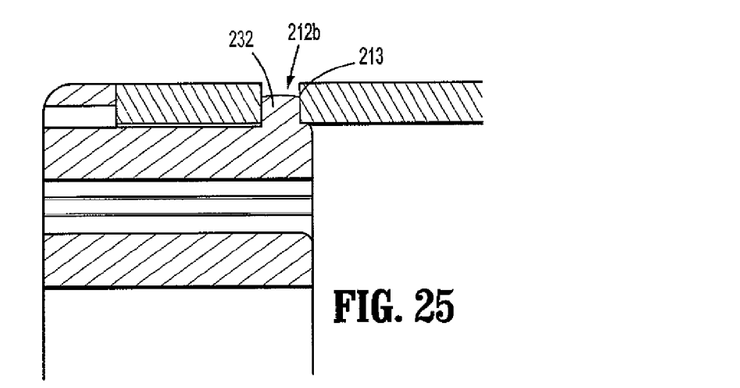
FIG. 25 is a cross sectional view taken along line 25-25 of FIG. 24.

In the alternate embodiment of FIGS. 18-20, flexible engagement bumps are provided. Staple guide 170 is identical to staple guide 60 of FIG. 2 and shell 180 is identical to shell 31 of FIG. 2 except for the structure cooperating with the hooks of the staple guide and the flexible bumps. More specifically, staple guide 170 has a flexible hook 172 extending proximally. Shell 180 has a locking aperture 182 dimensioned and configured to receive the hook 172. Hook 172 flexes as it is inserted past wall 183 positioned distal of locking aperture 182. The distal end of the wall 183 preferably has an angled surface 185 cooperating with the angled surface 174 of hook 172 to facilitate insertion. During assembly, wall 183 biases hook 172 radially inwardly in a similar fashion as hook 84 of FIG. 2 to enable it to pass proximally beyond wall 183, and then the hook 172 returns to its normal position received in locking aperture 182 as shown in FIG. 20. During use, a distal force applied to staple guide 170 will not dislodge the staple guide 170 from shell assembly 180 since distal movement is prohibited by engagement of shoulder 175 with wall 189.

Shell 180 can also have a series of flexible bumps or projections 186 to enhance securement of the staple guide 170. Bumps 186 extend distally from distal edge 187 of shell 180. When the staple guide 170 is attached to the shell 180, the flexible bumps or projections 186 are pressed inwardly. As a result, after assembly, the bumps 186 provide a distal force on the staple guide 170, thereby forcing hook 172 (shoulder 175) distally against surface 189 of wall 183 to the extent there is any slack between the shoulder 175 of hook 172 and the wall 189 adjacent locking aperture 182 when assembled. Consequently, the bumps/projections 186 function similar to a spring biasing the staple guide 170 in a distal direction when assembled to the shell 180. It should be appreciated that the bumps or projections can be provided on the other embodiments of the shell disclosed herein to provide a distal biasing force if desirable.

FIGS. 21-27 illustrate another alternate embodiment for attaching the staple guide to the shell assembly utilizing a bayonet mount. Shell 210 is identical to shell 31 of FIG. 2 except for the structure cooperating with the tabs of the staple guide. More specifically, shell 210 has a slotted region 212. Slotted region 212 extends proximally from a distal edge 214 of the shell 210 in a longitudinal (axial) direction forming an axial slotted region 212a of slot 212. Slot 212 also has a radially extending region 212b transverse to the axial region 212a, thereby forming a substantially L-shape slotted configuration. A blocking indentation 213 extends into radial region 212b. For ease of explanation blocking recess or indentation 213 can be considered as dividing radial region 212b into two sections.

Figure 2:
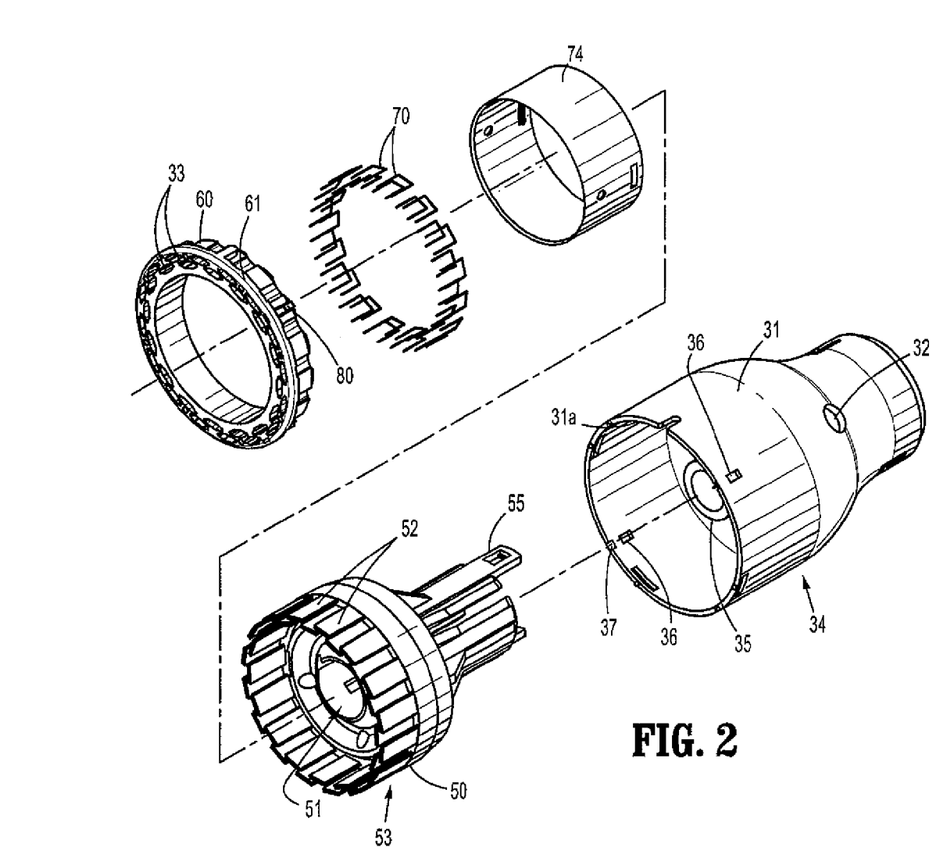
FIG. 2 is an exploded view of the shell assembly of the stapling instrument of FIG. 1.
Figure 3:
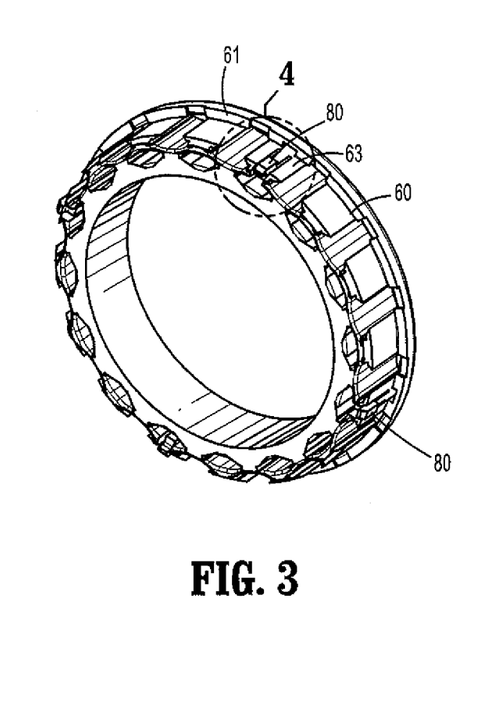
FIG. 3 is an enlarged view of the staple guide of FIG. 2.
Figure 4:
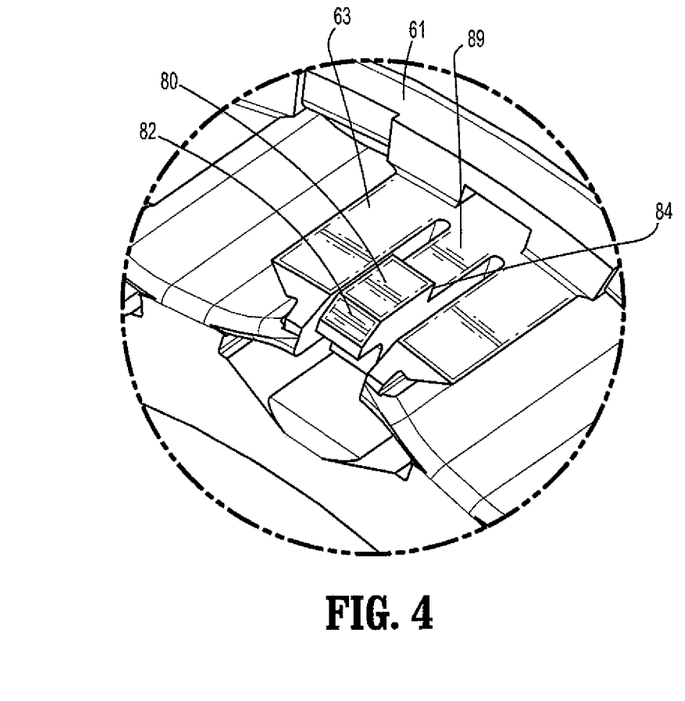
FIG. 4 is an enlarged view of the area of detail designated in FIG. 3 illustrating the flexible hook of the staple guide.
Figure 26:
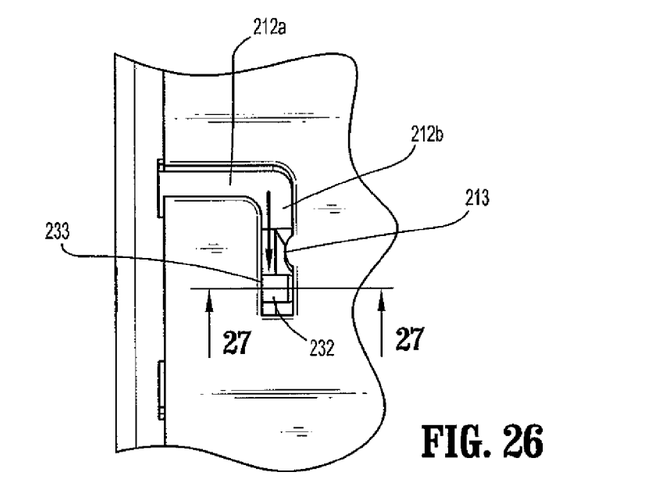
FIG. 26 is a close up view of the locking tab of FIG. 23 in the locking position within the slot of the shell.
Figure 27:
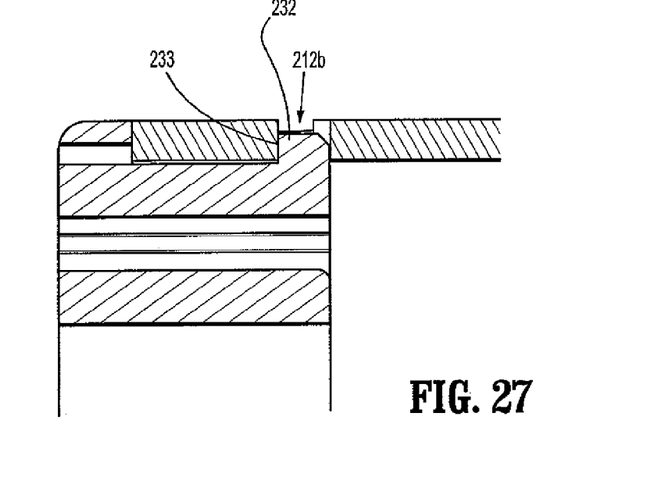
FIG. 27 is a cross sectional view taken along line 27-27 of FIG. 26.

Staple guide 230 is identical to staple guide 60 of FIG. 2 except for the structure engaging the shell 210 for attachment thereto. More specifically, staple guide 230 has a locking tab 232 at a proximal edge 234. As can be appreciated by viewing FIGS. 23-27, when staple guide 230 is attached during assembly to the shell assembly 110 by placement in a direction of arrow E, the locking tab 232 enters the axial region 212a of slot 212. After the locking tab 232 is inserted to the edge 212c of axial region 212a (see FIG. 23), staple guide 230 is then rotated and the tab 232 is moved in the radial region 212b of slot 212 in the direction of arrow F of FIG. 24. Rotation continues until tab 232 is forced past blocking recess 213 as shown in FIG. 26. That is, as tab 232 moves along the radial region 212b of slot 212, it is forced past locking recess 213 which forms a reduced diameter region 212f of region 212b of slot 212 (The region 212f has a smaller dimension than a transverse dimension of the locking tab 232). Once moved past this reduced diameter region 212f, the region prevents withdrawal of the locking tab 232, i.e. movement in the direction opposite the direction of arrow F, unless a sufficient force is applied by rotation of the shell guide 230 to overcome the blocking recess (indentation) 213 and pass by the reduced diameter region. Note that the structure can be provided so that either the tab 232 flexes or the indented wall forming the blocking recess 213 flexes so the tab can move past the indentation. During use, a distal force applied to the staple guide 230 during manipulation of the instrument or firing of the staples will not dislodge the staple guide 230 from the shell assembly 210 since distal movement is prohibited by wall 233 and disconnection requires reverse rotation of the staple guide 230 to remove it from the slot 212.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

What is claimed:

1. A surgical instrument, comprising:
   a handle assembly;
   an elongated body portion extending distally from the handle assembly;
   a head portion disposed adjacent a distal portion of the elongated body portion and including an anvil assembly and a shell assembly, the shell assembly including a shell and a staple guide, the staple guide configured to house a plurality of staples in an annular array, the shell including a locking aperture formed in an outer surface of the shell spaced proximally of a distal end of the shell and defining a proximal wall and a distal wall, the shell including a ramp;
   a pusher positioned at least partially within the shell and advanceable relative to the staple guide; and
   a flexible engagement feature including at least one hook disposed on the staple guide, the hook including an angled surface disposed adjacent a proximal end thereof, and wherein the angled surface of the hook slidably contacts the ramp of the shell upon engagement between the staple guide and the shell and prior to the hook engaging the locking aperture.

2. The instrument of claim 1, wherein the flexible engagement feature includes a flexible tab on the shell.

3. The instrument of claim 2, wherein the locking aperture of the shell in formed on the flexible tab.

4. The instrument of claim 1, wherein the hook is substantially rigid.

5. The instrument of claim 2, wherein the flexible tab is positioned adjacent a distal-most end of the shell.

6. The instrument of claim 1, further comprising at least one flexible projecting member compressible by the staple guide.

7. The instrument of claim 1, wherein the shell assembly includes a plurality of projections extending distally to apply a distal force to the staple guide.

8. The instrument of claim 7, wherein the projections are compressible by the staple guide.

9. The instrument of claim 7, wherein the projections extend from a distal most end of the shell.

10. The instrument of claim 1, wherein the staple guide has a flange annularly disposed thereon, and wherein the hook is positioned proximal of the flange.

11. instrument of claim 1, wherein the hook is substantially flush with an outer surface of the staple guide.

12. The instrument of claim 1, wherein the flexible engagement feature comprises first and second hooks radially disposed on the staple guide, the first and second hooks configured to engage first and second locking apertures of the shell assembly.

13. The instrument of claim 12, wherein the first and second hooks are spaced approximately 180 degrees apart.

14. The instrument of claim 1, wherein the hook has a shoulder engageable with a surface of a distal wall defined by the locking aperture.

15. The instrument of claim 1, wherein the hook does not extend radially outward of a radial outer surface of the shell.

16. The instrument of claim 1, wherein a distal shoulder of the hook engages a distal wall defined by the locking aperture.

* * * * *